(12) United States Patent
Fitzmaurice

(10) Patent No.: US 6,344,597 B1
(45) Date of Patent: Feb. 5, 2002

(54) INTERSPECIFIC NICOTIANA HYBRIDS AND THEIR PROGENY

(75) Inventor: Wayne P. Fitzmaurice, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 09/353,787

(22) Filed: Jul. 15, 1999

Related U.S. Application Data

(63) Continuation-in-part of application No. 09/232,170, filed on Jan. 15, 1999, which is a continuation-in-part of application No. 09/008,186, filed on Jan. 16, 1998.

(51) Int. Cl.⁷ .......................... A01H 1/00; A01H 5/00; C12Q 1/68; C12N 5/00; C07H 21/02
(52) U.S. Cl. .................. 800/269; 800/298; 435/6; 435/410; 435/468
(58) Field of Search ................. 800/260, 265, 800/266, 268, 269, 274, 317.3; 435/6, 69.1, 91.1, 468, 375; 536/23.1

(56) References Cited

U.S. PATENT DOCUMENTS

| | | | | |
|---|---|---|---|---|
| 4,827,079 A | * | 5/1989 | Evans et al. .................. 800/1 |
| 5,177,306 A | * | 1/1993 | Whitaker ................. 800/317.3 |
| 5,316,931 A | | 5/1994 | Donson et al. ................ 435/6 |
| 5,589,367 A | | 12/1996 | Donson et al. ................ 435/6 |
| 5,811,653 A | | 9/1998 | Turpen ....................... 800/205 |
| 5,824,856 A | * | 10/1998 | Mori et al. .................. 800/278 |
| 5,866,785 A | | 2/1999 | Donson et al. .............. 800/205 |
| 5,928,406 A | * | 7/1999 | Salt et al. ..................... 75/712 |
| 5,998,710 A | * | 12/1999 | Stangland ................ 800/320.1 |

OTHER PUBLICATIONS

Bu, G..Z.. et al. "Investigation on genetic traits and selection of interspecific somatic hybrid progenies in tobacco," 1989, pp. 213–22, *Chin J. Biotechnol* (Abstract of article).

Kung, S.D. et al. "The evolution of fraction i protein during the origin of a new species of Nicotiana," 1975, pp. 59–64, *J Mol. Evol* (Abstract of article).

GRIN printout for *Nicotiana excelsior* (Abstract from database).

GRIN printout for *Nicotiana benthamiana* (Abstract from database).

Smith, H.H. "The Genus as a Genetic Resource." pp. 1–3, 6–16, *Technical Bulletin 1586*, USDA.

Burk, L.G., et al. "Hybridization." pp.23–27, *Technical Bulletin 1586*, USDA.

Campbell, K.G., et al. "Construction of a designer chromosome in tobacco," 1994, pp. 837–842, *Theor. Appl. Genet.*

\* cited by examiner

*Primary Examiner*—John L. LeGuyader
*Assistant Examiner*—Jane Zara
(74) *Attorney, Agent, or Firm*—Rothwell, Figg, Ernst & Manbeck

(57) ABSTRACT

The present invention relates to novel interspecific *Nicotiana excelsior×N. benthamiana* hybrid seeds and plants and to a method of producing interspecific Nicotiana hybrids having enhanced properties for biomass and the production of recombinant proteins using a viral vector system.

55 Claims, No Drawings

INTERSPECIFIC NICOTIANA HYBRIDS AND THEIR PROGENY

CROSS-REFERENCE TO RELATED APPLICATIONS

This application is a continuation-in-part of application Ser. No. 09/232,170 filed on Jan. 15, 1999, which in turn is a continuation-in-part application of Ser. No. 09/008,186 filed on Jan. 16, 1998, each incorporated herein by reference.

BACKGROUND OF THE INVENTION

The present invention relates to novel interspecific *Nicotiana excelsior*×*N. benthamiana* hybrid seeds and plants and to a method of producing interspecific Nicotiana hybrids having enhanced properties for biomass and the production of recombinant proteins using a viral vector system.

The difference between intra- and interspecific hybrids can be visualized by the Mendelian behavior of intraspecific hybrids and the essentially non-Mendelian behavior of interspecific hybrids. This difference results from the complete chromosome homology in hybrids between plants of the same species (intraspecific) and the partial or nonchromosome homology that characterizes hybrids between plants of different species (interspecific). The intermediate or gray area between the extremes among interspecific hybrids is seen in the behavior of those involving closely related species. Such species will have the same chromosome number, and the extent of chromosome homologies may be very high. Hybrids of this kind produce seed when self-pollinated and show evidence of Mendelian patterns of segregation for some traits.

Cytological studies of meiosis in some $F_1$ hybrids may show evidence of chromosome irregularities that reflect the chromosomal differences that mark the parents as different species. A hybrid between distantly related species may show reduced pairing between chromosomes of the different genomes. Meiosis in such hybrids may exhibit the typical chromosome behavior characteristic of monogenomic haploids. Most interspecific $F_1$ hybrid combinations in the genus Nicotiana fall into this latter category. Their chromosome doubled counterparts are called amphidiploids, or simply allopolyploids, when a parent of the hybrid may itself be a combination of different ancestral genomes. *N. tabacum* represents a typical example.

The relative difficulty of producing interspecific $F_1$ hybrids increases in proportion to the decrease in taxonomic relations between their parents. Although some $F_1$ hybrids are stable when converted to fertile polyploids, even hybrids between distantly related parents share some degree of chromosome homology. There are advantages to maintaining seed stocks of allopolyploids by self-pollination, particularly if the hybrid is difficult to obtain by conventional cross-pollination.

Interspecific hybridization and introgression in natural populations of plants and animals is a known source of genetic variation and adaptation. The term introgression, or introgressive transfer, of genetic traits is used in a narrower sense with short-term breeding projects. The goal of experimental interspecific hybridization is usually the introgressive transfer of a specific trait from one species (the nonrecurrent parent) into the genome of another (the recurrent parent). The trait must be expressed with reasonable phenotypic fidelity as a dominant or partial dominant in the $F_1$ hybrid and all subsequent backcross generations, when nonrecurrent chromosomes are lost at random, otherwise the proposed interspecific transfer could not be made. Foreign genes from one species can become unstable when translocated into the germplasm of another.

Chromosome pairing between the foreign genomes in an interspecific hybrid may be extensive or minimal although the $F_1$ hybrid is usually sterile. Fertility may be restored by treating germinating seed of the hybrid in 0.4 percent aqueous colchicine for about 4 hours to induce chromosome doubling. Immersion of the seeds in 0.1 percent colchicine for 24 hours may also be effective. Thereafter, the seed is rinsed in sterile distilled water and planted by sowing on the surface of pasteurized soil in glass or plastic preparation dishes. The seedlings later are transplanted to pots of soil in the greenhouse and mature plants that show good pollen development are self pollinated or backcrossed to the recurrent parent.

Three conventional approaches to interspecific hybridization for the purpose of alien transfer and incorporation of germplasm into stable diploid lines are (a) diploid×diploid then doubling to produce the allopolyploid and backcrossing to produce the sesquidiploid, (b) autotetraploid×autotetraploid to produce the allopolyploid directly, and © autotetraploid×diploid to produce the sesquidiploid directly as described in Technical Bulletin 1586, U.S. Department of Agriculture, 1979.

Gene transfer mediated by *Agrobacterium tumefaciens* vectors has become routine in tobacco (DeBlock et al., 1987; Grierson, et al., 1990; Hilder, et al., 1990; Lindbo and Dougherty, 1992). Commercial use of genetic transformation in agriculture depends on the incorporation of foreign genes into high-yielding germplasm. Plant breeders may want to combine several foreign genes into a single elite germplasm source. In order to accomplish this goal, designer chromosome construction is desirable.

Designer, or artificial, chromosomes have been produced in yeast. In plants, the scaffold for designer chromosome construction can be found in a breeding line that possesses the full complement of chromosomes from its own species plus an additional chromosome from a related species, Campbell, et al., Construction of a designer chromosome in tobacco, *Theor Appl Genet* (1994) 87:837–842. Additional chromosomes are often meiotically stable as homozygotes, and because recombination between additional chromosomes and the rest of the plant genome is rare (Gerstel 1945) the integrity of a foreign-gene linkage package can be preserved.

The placement of this linkage package on an additional chromosome will also minimize disturbance to the rest of the plant genome. The genetic structure of high-yielding germ plasm can be disturbed either through insertional mutagenesis or the disturbance of beneficial linkage blocks. Insertional mutagenesis, caused by the integration of foreign genes into plant coding sequences, can occur frequently. Konez, et al. (1989) estimated that at least 30% of all T-DNA insertions occur in transcribed regions of the Arabidopsis and Nicotiana genomes. Beneficial linkage blocks are formed through intermating and recombination followed by selection.

The desired traits for a plant may not be present in the germplasm of the species of interest. In such a case, traditional breeding within the species may not give acceptable results. Introducing a desired trait from one species into a related one by interspecific hybridization is followed by introgression into the recurrent parent.

Methods for expressing genes in plants has been described in U.S. Pat. Nos. 5,316,931; 5,589,367; 5,811,653 and 5,866,785, all of which are incorporated herein. Certain species have either an acceptable biomass or an acceptable expression of a sequence inserted into a plant viral vector, but no current species have both high levels of biomass and high levels of viral vector performance. There is a need for a method to develop in one species both the characteristics of increased biomass and improved viral vector performance.

SUMMARY OF THE INVENTION

The present invention is directed to a method of crossing two different species of Nicotiana to produce an interspecific hybrid which results in an increased biomass and improved host susceptibility to a viral vector.

In accordance with this invention, interspecific Nicotiana hybrids have been produced that are characterized with having a biomass of greater than that usually obtained from tobacco with CP-fusion constructs and a virion yield of greater than 1.0 mg. virion/gram fresh weight.

In one embodiment of the invention, there is provided a novel Nicotiana interspecific hybrid. This invention thus relates to the seeds of Nicotiana interspecific hybrid, to the plants of Nicotiana interspecific hybrid and to methods for producing a Nicotiana interspecific hybrid plant produced by crossing the Nicotiana interspecific hybrid with itself or another Nicotiana interspecific hybrid line.

Thus, any such methods using the Nicotiana interspecific hybrid are part of this invention: selfing, backcrosses, hybrid production, crosses to populations, and the like. All plants produced using a Nicotiana interspecific hybrid as a parent are within the scope of this invention. Advantageously, the Nicotiana interspecific hybrid could be used in crosses with other, different, Nicotiana interspecific hybrids to produce first generation ($F_1$) Nicotiana interspecific hybrid seeds and plants with superior characteristics.

In another aspect, the present invention provides for single gene converted plants of Nicotiana interspecific hybrid. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring Nicotiana gene or a transgene introduced through genetic engineering techniques.

In another aspect, the present invention provides regenerable cells for use in tissue culture of a Nicotiana interspecific hybrid. The tissue culture will preferably be capable of regenerating plants having the physiological and morphological characteristics of the foregoing Nicotiana interspecific hybrid, and of regenerating plants having substantially the same genotype as the foregoing Nicotiana interspecific hybrid. Preferably, the regenerable cells in such tissue cultures will be embryos, protoplasts, meristematic cells, callus, pollen, leaves, anthers, roots, root tips, flowers, seeds, pods or stems. Still further, the present invention provides Nicotiana plants regenerated from the tissue cultures of the invention.

DETAILED DESCRIPTION OF THE INVENTION

To provide an understanding of several of the terms used in the specification and claims, the following definitions are provided:

Geneware™ viral vector—As used herein, Geneware™ viral vector refers to a system for expressing genes in plants, such as described in U.S. Pat. Nos. 5,316,931; 5,589,367; 5,811,653 and 5,866,785, all incorporated herein by reference.

Biomass—As used herein, the term "biomass" means the total fresh weight in rams of plant tissue which is harvested above the ground. The terms "fresh weight" and "biomass" are used interchangeably herein.

Virion yield—As used herein the term "virion yield" means the total yield of the virus measured in mg of virion per gram fresh weight.

Host—As used herein, a "host" means a cell, tissue or organism capable of supporting replication of a vector or plant viral nucleic acid and which is capable of being infected by a virus containing the viral vector or plant viral nucleic acid.

Infection—As used herein, an "infection" means the ability of a virus to transfer its nucleic acid to a host or introduce viral nucleic acid into a host, wherein the viral nucleic acid is replicated, viral proteins are synthesized, and new viral particles assembled. In this context, the terms "transmissible" and "infective" are used interchangeably herein.

Phenotypic Trait—As used herein, "phenotypic trait" is an observable property resulting from the expression of a gene or genes.

Plant Tissue—As used herein, "plant tissue" is any tissue of a plant in planting or in culture. This term is intended to include a whole plant, plant cell, plant organ, protoplast, cell culture, or any group of plant cells organized into a structural and functional unit.

Recombinant Plant Viral Nucleic Acid—As used herein, "recombinant plant viral nucleic acid" means it has been modified to contain nonnative nucleic acid sequences.

Recombinant Plant Virus—As used herein, "recombinant plant virus" is a plant virus containing the recombinant plant viral nucleic acid.

Vector—As used herein, "vector" is a self-replicating nucleic acid molecule which transfers a nucleic acid segment between cells.

Virus—As used herein, "virus" is an infectious agent composed of a nucleic acid encapsidated in protein. A virus may be a mono-, di-, tri- or multi-partite virus.

Backcrossing—As used herein, "backcrossing" is a process in which a breeder repeatedly crosses hybrid progeny back to one of the parents, for example, a first generation hybrid $F_1$ with one of the parental genotypes of the $F_1$ hybrid.

Essentially all the physiological and morphological characteristics—As used herein, a plant having essentially all the physiological and morphological characteristics means a plant having the physiological and morphological characteristics, except for the characteristics derived from the converted gene.

Single Gene Converted (Conversion)—As used herein, "single gene converted (conversion)" plant refers to plants which are developed wherein essentially all of the desired morphological and physiological characteristics of a variety are recovered in addition to the single gene transferred into the variety via the backcrossing technique or via genetic engineering.

Trichomes—As used herein, "trichomes" means the glandular hairs on the surface of the plant stem, leaf, calyx, corolla or other plant tissue surfaces.

Leaf lamina—As used herein, "leaf lamina" means the leaf surface devoid of vascular tissue of primary, secondary or ternary nature.

GFP-GJ—As used herein, "GFP-GJ" means a crude plant extract containing green fluorescent protein.

GFP-pH5, Δ—As used herein, "GFP-pH5, Δ" means a crude plant extract that was treated with heat and a pH of 5 that contains green fluorescent protein that is enriched for its presence.

CP-GJ—As used herein, "CP-GJ" means a crude plant extract containing viral coat protein.

CP-pH5, Δ—As used herein, "CP-pH5, Δ" means a crude plant extract that was treated with heat and a pH of 5 that contains coat protein that is enriched for its presence.

Host plant species vary in their ability to support expression of a sequence inserted into a plant viral vector. For example, some species (such as Nicotiana benthamiana) support expression from a dual-subgenomic promoter tobamoviral vector to a high specific activity, but have relatively low biomass. Other species (such as N. tabacum) have high biomass and/or other desirable properties for growth in the field, but have a relatively low specific activity of the expressed protein. Using the method of the present invention, after chromosome doubling to restore fertility, the primary hybrid may have suitable properties, or it may be desirable to backcross toward either parent selecting or screening at each generation for the desired properties of the non-recurrent parent (e.g., introgressing the superior biomass of N. tabacum into N. benthamiana, or introgressing the superior viral vector performance of N. benthamiana into N. tabacum). A viral vector expressing the green fluorescent protein (GFP) is one example of a useful tool for screening the level of systemic expression in candidate hybrid plants. Geneware™ viral vector refers to a system for expressing genes in plants such as described in U.S. Pat. Nos. 5,316,931; 5,589,367; 5,811,653 and 5,866,785, all incorporated herein by reference.

EXAMPLES

The following examples are provided to further illustrate the present invention and are not intended to limit the invention beyond the limitations set forth in the appended claims.

Example 1

Procedures for Making Interspecific Crosses of Nicotiana

When making interspecific crosses it is important to have: 1) healthy plants, 2) careful emasculation, 3) freedom from contamination by foreign pollen, 4) a reasonable level of cross fertility among the parent plants, and 5) recording of the crosses. A pair of fine curved-point forceps is used to slit the corolla and emasculate the blossom. In the case of N. tabacum, and many other species, the anthers are removed just before the corolla unfolds. Several exceptions apply to this general rule. In the case of N. repanda, the anthers are adnate to the stigma, the anther walls usually break down, and the contents of the anther adhere to the stigma before the flower matures. Anthers in the later-formed flowers of N. nudicaulis may dehisce before the corolla unfolds and self-pollination will occur. The flowers of these species are emasculated several days before cross-pollinations are made.

Ordinarily, pollinations are made immediately after emasculation, up to 18 to 24 hours after emasculation before applying pollen. The glistening and sticky surface of the stigma is touched with a newly dehisced anther, or pollen may be applied with the aid of a small artist's brush (size 6/128 to 10/128). Brush pollination aids seed set in some self-fertile species, and sib-pollinations are required to produce seed of self-sterile species. The brush used to transfer pollen is inserted between siblings, handle down, in a pot. Inexpensive brushes with plastic handles are preferable to those with wooden handles as microorganismal activity will cause the latter to rot. If pollen of a desired parent is unavailable from living plants, use pollen that was collected at an earlier time and stored frozen in gelatin capsules. Gwynn has found that frozen pollen from N. tabacum may remain viable for as long as 7 years.

If a parental plant is suspected of harboring a mechanically transmitted virus, the instruments are sterilized in 70 percent ethanol. After a pollination has been made, a length of drinking straw, slightly longer than the pistil, is placed over the stigma and crimped by folding to prevent contamination by self- or foreign-pollen. Use of straws is probably unnecessary if plants are well spaced on the greenhouse bench, mature blossoms are removed, and neither insects nor excessive air movements present a problem. Furthermore, under most circumstances, a stigma thoroughly covered with the intended pollen offers sufficient protection against contamination. Usually, fertilization is affected within 1 to 2 days. Mark individual crosses with a small, stringed key tag. Moisten the string before looping it around the pedicel otherwise the flower may be severed when the string is tightened. Whenever a number of identical crosses are planned, time can be saved by marking the tags in advance of pollination.

Generally, seed of most Nicotiana spp. will mature about 28 days after pollination. Seedlings of N. tabacum may be obtained earlier by scraping the developing seeds from the carpels about 18 days after pollination and treating them in 0.5 percent sodium hypochlorite (Clorox and water, 1:9) for about 10 minutes. One or two capsules of N. tabacum will contain enough seed to maintain a breeding line, but the seed yield per capsule of other species may be considerably smaller.

Some Nicotiana spp. are essentially day neutral whereas others require special temperature and day-length conditions to initiate flowering. Therefore, when planning specific hybridizations, consider the day-length requirements of the species involved, unless you can freeze pollen for use at a later time. Certain crosses may require a multitude of individual pollinations with the hope of obtaining a single seed among many mature capsules, for example, the cross diploid N. rustica×diploid N. tabacum. Difficult hybridizations may yield a paucity of shrunken seed of a smaller than average size. Although most seeds of this kind are often inviable, some of them may be induced to germinate if they are sown on soil in covered plastic or glass preparation dishes. when seeds are limited in number, do not treat the seedlings with colchicine. Selecting the most vigorous plants is better for asexual propagation. Later, treat the growing points of the clonal material with 0.5 percent aqueous colchicine three times a day for 3 days to induce chromosome doubling.

Premature blossom drop may be avoided by the use of 0.5 percent indoleacetic acid in lanolin. Apply it by dipping a needle into the preparation and scratching the pedicel at its point of attachment. This treatment will cause the blossom to remain on the plant regardless of embryo development and, therefore, offers no guarantee of a successful hybridization. On the other hand, syngamy serves to prevent abscission.

Example 2

Selection of Parental Lines for *N. excelsior/N. benthamiana* Hybrids

Seven accessions of *N. excelsior* were collected. All of the accessions had similar characteristics, but only TW46 and TW47 were determined to be good hosts for GFP Geneware™ viral vector. TW46 was identified as a poor host for certain insert genes in Geneware™ viral vector. Since systemic necrosis was observed in TW46, TW47 was selected. A group of over 100 *N. excelsior* TW47 were inoculated to give a statistically valid survey of the performance of GFP Geneware™ viral vector on *N. excelsior*. Almost all of the plants gave good-to-excellent systemic GFP expression. A virus preparation from 200 grams of infected whole plants gave a final yield of 2 mg virion/g fresh weight. Unexpectedly this was 5- to 10-fold higher than the virion yield typically obtained from tobacco with CP-fusion constructs. The higher virion yield for *N. excelsior* when extended to the field, the yield per acre would be similar to tobacco, but the amount of tissue (waste) in the bioprocessing stream is greatly reduced. Typical results for *N. benthamiana* are 0.9 mg virion/g fresh weight.

Seven accessions of *N. benthamiana* were screened for biomass and as a host for systemic expression from dual-subgenomic Geneware™ viral vector. One of the best performers was TW16.

Example 3

A primary interspecific hybrid between *N. excelsior* TW47 and *N. benthamiana* TW16 gave very good systemic GFP expression with GFP Geneware™ viral vector. Midvein regeneration was performed to stimulate chromosome-doubling and restoration of fertility (References: Campbell et al., Theor Appl Genet 87 (1994) 837–842; Kasperbauer and Collins, Crop Sci 12 (1972) 98–101). TW47 and TW16 Accessions were each obtained from the USDA Tobacco Germplasm Collection in Oxford, N.C. Currently this collection is curated by Verne A. Sisson, Department of Crop Science, North Carolina State University, Raleigh, N.C. 27695 (Phone: 919/693-5151, ext. 228).

Several regenerants set seed indicating chromosome-doubling and restored fertility. The working name for the hybrid species is *N. excelsiana*. The seed was germinated, and the resulting plants were evaluated for biomass and systemic Geneware™ viral vector expression. Systemic GFP expression was near the level of *N. benthamiana*. Biomass and growth habit were similar to *N. excelsior*.

Plants were grown in Kentucky for an agronomic test. The plants survived well in the field (better than the *N. benthamiana*) and showed some bluemold resistance. Biomass was intermediate between the parental values.

The primary chromosome-doubled hybrid between *N. excelsior* and *N. benthamiana* (*N. excelsiana*) appears to be a stable true-breeding line. It has good biomass and excellent Geneware™ viral vector properties, and did well in a test in Kentucky.

In Table 1 listed below the phenotypic observations for several traits are shown for two lines each of the parents *Nicotiana benthamiana* TW16; *Nicotiana excelsior* TW47 and the hybrid *Nicotiana excelsiana* 7.b.

TABLE 1

Phenotypic Observations
Planted 3/10/99; Data Collected 4/22/99

| Traits | *Nicotiana benthamiana* | | *Nicotiana excelsior* | | *Nicotiana excelsiana* | |
|---|---|---|---|---|---|---|
| | TW16 #1 | TW16 #2 | TW47 #1 | TW47 #2 | 7.b #1 | 7.b #2 |
| First flower open | 4/23/99 | 4/22/99 | Budding | Budding | Budding | Budding |
| Height (to top of stem) | 20 cm | 26 cm | 27 cm | 20 cm | 34 cm | 26 cm |
| Largest leaf (Length) | 18 cm | 19.5 cm | 17–20 cm | 19.5 cm | 21 cm | 19 cm |
| Largest leaf (Width) | 13 cm | 13.5 cm | 10–12 cm | 10 cm | 14 cm | 13 cm |
| Leaf shape | Round | Round | Oblong | Oblong | Oval | Oval |
| Leaf angle | 90° | 90° | 90° | 90° | 90° | 90° |
| Leaf color | Med. green | Med. green | Dark green | Dark green | Med. green | Med. green |
| Trichomes | Mod. #, small | Mod. #, small | Few, large | Few, large | Few, large | Few, large |
| Petiole leaf | No | No | Yes, 70–80 mm | Yes, 40 mm | Yes, 20 mm | Yes, 14 mm |
| Petiole length | 5 cm | 6 cm | Continuous w/ leaf lamina | Continuous w/ leaf lamina | 6 cm | 5 cm |
| Leaf lamina | 13 × 13 cm | 13.5 × 13.5 cm | 20 × 12 cm | 19.5 × 10 cm | 15 × 14 cm | 14 × 13 cm |
| Internode length | 10 mm | 15 mm | 15 mm | 15 mm | 22 mm | 21 mm |
| Stalk diameter | 7 mm | 7 mm | 7 mm | 8 mm | 7 mm | 7 mm |
| Branching | Yes @ every leaf node | Yes @ every leaf node | Yes, barely from 5 leaf nodes | Not yet | Yes, 2 nodes starting to extend | Yes, 2 nodes starting to extend |
| Flower form | Nb | Nb | | | | |
| Flower color | White | White | | | | |
| Flower head habit | 1 flower/leaf node on main stem | 1 flower/leaf node on main stem | | | | |

TABLE 2

Phenotypic Observations
Planted 3/10/99; Data Collected 4/26/99

| | Nicotiana benthamiana | | Nicotiana excelsior | | Nicotiana excelsiana | |
|---|---|---|---|---|---|---|
| Traits | TW16 #1 | TW16 #2 | TW47 #1 | TW47 #2 | 7.b #1 | 7.b #2 |
| First flower open | Yes, secondary meristems starting bud | Yes, secondary meristems starting bud | 4/25/99 Buds on topmost branches | 4/25/99 Buds on topmost branches | 4/25/99 Buds on topmost branches | Budding; Estd opening 4/28/99 |
| Height (to top of stem) | 24 cm | 31 cm | 40 cm | 31 cm | 49 cm | 40 cm |
| Largest leaf (Length) | 21 cm | 21 cm | 21 cm | 21 cm | 23 cm | 22 cm |
| Largest leaf (Width) | 15 cm | 15 cm | 14 cm | 11.5 cm | 15.5 cm | 13.7 cm |
| Leaf shape | Round | Round | Oblong | Oblong | Oval | Oval |
| Leaf angle | 90° | 90° | 90° | <90° | 90° | 90° |
| Leaf color | Med. green | Med. green | Dark–med. green | Med. green | Med. green | Med. green |
| Trichomes | Small, med. # | Small, med. # | Few, large | Few, large | Few, large | Few, large |
| Petiole leaf | No | No | Yes, 9.5 cm | Yes, 4 cm | Yes, 20 mm | Yes, 18 mm |
| Petiole length | 5 cm | 6 cm | N/A | N/A | 7 cm | 5.5 cm |
| Leaf lamina | 16 × 15 cm | 15 × 15 cm | 21 × 14 cm | 21 × 11.5 cm | 16 × 15.5 cm | 16.5 × 13.7 cm |
| Internode length | 1.6 cm (10 nodes) | 2 cm (10 nodes) | 3.2 cm (5 nodes) | 2.9 cm (5 nodes) | 3 cm (8 nodes) | 2.4 cm (10 nodes) |
| Stalk diameter | 7 mm | 8 mm | 8 mm | 7 mm | 8 mm | 8 mm |
| Branching | Yes, almost all leaf nodes | Yes, almost all leaf nodes | Yes, 5 are extending | Yes, 5 are extending | Yes, 9 are extending | Yes, 6 are extending |
| Flower form | Nb | Nb | Large | Large | Medium | N/A |
| Flower color | White | White | White | White | White | N/A |
| Flower head habit | 1/node from main stalk | 1/node from main stalk | 1/node from main stalk | 1/node from main stalk | 1/node from main stalk | N/A |

TABLE 3

| Plant | GFP-GJ | GFP-pH 5, Δ | CP-GJ | CP-pH 5, Δ |
|---|---|---|---|---|
| *N. benthamiana* lab strain | 0.5 mg/g FW | 0.6 mg/g FW | 1.1 mg/g FW | 1.6 mg/g FW |
| *N. tabacum* MD609 | ND | ND | ND | ND |
| BB/TT hybrid | 0.2 | 0.1 | 0.2 | 0.1 |
| *N. benthamiana* TW16 | 1.0 | 0.8 | 1.4 | 1.2 |
| *N. excelsior* TW47 | 1.2 | 0.8 | 2.6 | 2.4 |
| *N. excelsiana* | 0.8 | 0.6 | 1.9 | 2.2 |
| *N. occidentalis* TW91 | 0.4 | 0.6 | 1.5 | 1.7 |
| *N. umbratica* TW144 | 0.9 | 0.9 | 1.0 | 1.0 |
| TW91 × TW144 | 0.5 | 0.5 | 0.8 | 0.9 |
| TW144 × TW91 | 0.7 | 0.6 | 1.3 | 1.3 |

Example 4

Backcross Progeny from Interspecific Hybrid TW47×TW16

Backcrosses to each parental type were performed in order to evaluate the characteristics of the sesquidiploids. The backcross to *N. excelsior* was the only one to germinate. They looked much like *N. excelsior* and gave a similar GFP expression pattern to *N. excelsior*. An additional backcross was performed to generate the first breakdown generation, and the resulting plants are currently being evaluated.

Example 5

In-field screening of various Nicotiana species was continued in 1999. The purpose of this study was to evaluate biomass differences between species, to evaluate growth characteristics differences between species, and to evaluate insect and disease pressure differences between species.

Nine different Nicotiana species were seeded in the greenhouse on April 14. Each species was seeded into three 72-cell trays and placed in a specially constructed float bed. Burley Gold growth media was used for the transplants. Trays were filled manually and dibbled using the Golf Ball Dibbler. Raw seed was used for eight of the species and pelleted Benthamiana seed was used for the lab strain Benthamiana transplants. The GROmore hand seeder was used to sow the raw seed and the pelleted seed was sown by hand. Each tray was labeled with a tray marker to identify each species. The pelleted lab strain Benthamiana trays were watered overhead for three days post-seedling to dissolve the clay pellet coating and facilitate cotyledon emergence. Table 4 outlines the species transplanted in this study.

TABLE 4

Nicotiana Species Transplanted

| Nicotiana Species | Species Identifier |
|---|---|
| TW 17 - *Nicotiana Benthamiana* | Harvested 12/8/97 |
| TW 16 - *Nicotiana Benthamiana* | Harvested 11/26/97 |
| SCR1 - *Nicotiana Benthamiana* | Harvested 11/6/98 |
| L3663 - *Nicotiana Benthamiana* | Harvested 4/9/98 |
| *Nicotiana Excelsiana* | Lot #7.b, Harvested 5/22/98 |
| *Nicotiana Occidentalis Obliqua* | Unknown SCRI Stock |
| TW 47 - *Nicotiana Excelsior* | Harvested 3/31/98 |

TABLE 4-continued

Nicotiana Species Transplanted

| Nicotiana Species | Species Identifier |
|---|---|
| TW 91 - *Nicotiana Occidentalis* | Harvested 12/16/97 |
| Lab Strain - *Nicotiana Benthamiana* | Lot #28b 29b RC |

Transplants were treated, through the float water, with the fungicide Ridomil. An insecticide, Orthene, and a foliar applied fungicide, Dithane were also applied to the transplants. At 21 DPT, fertilizer was applied to the float water. A fertility level of 7 on the DiSST-4 meter was maintained throughout transplant production.

Transplants were transported to the ARP for transplanting on May 20, 37 DPS. Plants were transplanted on raised, black plastic covered beds, using a mechanical transplanter at a density of four plants per linear foot of bed. The plants were transplanted in two rows on the bed with an offset plant configuration. The transplant water contained ½ gallon of 7-14-7 Starter Fertilizer and ½ pound of Orthene per 150 gallons of water. Each species was replicated three times with each replication consisting of ten feet of bed.

At transplanting, several differences were apparent in transplant quality. TW 16 produced a slightly leggy transplant that wilted soon after transplanting. TW 17 transplants were smaller than the other Benthamiana transplants. However, TW 17 transplants had a thicker stem and appeared much hardier than the other Benthamiana transplants. The Lab Strain Benthamiana plants were much smaller and less consistent in plant size due to problems with germination during the transplant production phase. These problems were probably due to the fact that these seeds were pelleted. Some of the Obliqua transplants were already elongated at the time of transplanting. The highest quality transplants were the Excelsiana seedlings. These seedlings were very dark green in color, held a thick stem, and appeared to handle transplant stress much better than the other seedlings in this plot.

All plot replications were treated every 7–10 days with Orthene and Dithane at a rate of 1 teaspoon/gallon. Soil moisture was monitored using gypsum blocks that were buried about 4–5 inches in the beds. No irrigation was necessary for this plot due to the timely rainfall.

On June 29, 43 DPT, four plants from each replication were sampled for fresh weight determination. Table 5 illustrates the results for each replication.

TABLE 5

Fresh Weights for each Replication

| Species | Replication No. | Weight/Plant (g/plant) |
|---|---|---|
| TW 16 Benthamiana | 1 | 411.6 |
| TW 16 Benthamiana | 2 | 235.7 |
| TW 16 Benthamiana | 3 | 280.1 |
| TW 17 Benthamiana | 1 | 426.8 |
| TW 17 Benthamiana | 2 | 352.6 |
| TW 17 Benthamiana | 3 | Dead |
| SCRI Benthamiana | 1 | 326.3 |
| SCRI Benthamiana | 2 | 236.6 |
| SCRI Benthamiana | 3 | Dead |
| L3663 Benthamiana | 1 | 335.6 |
| L3663 Benthamiana | 2 | 292.1 |
| L3663 Benthamiana | 3 | Dead |

TABLE 5-continued

Fresh Weights for each Replication

| Species | Replication No. | Weight/Plant (g/plant) |
|---|---|---|
| TW 47 Excelsior | 1 | 616.5 |
| TW 47 Excelsior | 2 | 450.6 |
| TW 47 Excelsior | 3 | 517.8 |
| TW 91 Occidentalis | 1 | 528.8 |
| TW 91 Occidentalis | 2 | 399.8 |
| TW 91 Occidentalis | 3 | 449.2 |
| *Occidentalis Obliqua* | 1 | 141.9 |
| *Occidentalis Obliqua* | 2 | 620.6 |
| *Occidentalis Obliqua* | 3 | 809.7 |
| Excelsiana | 1 | 333.0 |
| Excelsiana | 2 | 512.4 |
| Excelsiana | 3 | 580.8 |
| Lab Strain Benthamiana | 1 | 90.5 |
| Lab Strain Benthamiana | 2 | 200.5 |
| Lab Strain Benthamiana | 3 | N/A |

Several replications died due to root rot induced by excess water surrounding the raised bed. This excess water came about due to excessive rainfall and poor plot drainage.

Table 6 summarizes the replication plant weights. The following Table 6 is the average of all replications for each species.

TABLE 6

Replication Averages by Species

| Species | Average Plant Weight (g/plant) |
|---|---|
| TW 16 Benthamiana | 305.8 |
| TW 17 Benthamiana | 389.7 |
| SCRI Benthamiana | 281.5 |
| L3663 Benthamiana | 313.9 |
| TW 47 Excelsior | 528.3 |
| TW 91 Occidentalis | 459.3 |
| *Occidentalis Obliqua* | 524.1 |
| Excelsiana | 475.4 |
| Lab Strain Benthamiana | 145.5 |

TW 17 performed well in comparison to the other Benthamiana in the plot. TW 17 was a very vigorous plant with excellent hardiness and high biomass levels. More work should be done to determine the feasibility of this plant as a viral vector host. Also, Excelsiana stood out as a superior plant in this plot. This plant offered high biomass levels with significant leaf size and weight.

This invention is also directed to methods for producing a Nicotiana plant by crossing a first parent Nicotiana plant with a second parent Nicotiana plant, wherein the first or second Nicotiana plant is the Nicotiana plant from the line Nicotiana Interspecific Hybrid. Further, both first and second parent Nicotiana plants may be from the cultivar TW47×TW16. Therefore, any methods using this cultivar are part of this invention: selfing, backcrosses, hybrid breeding, and crosses to populations. Any plants produced using cultivar as a parent are within the scope of this invention.

As used herein, the term "plant" includes plant cells, plant protoplasts, plant cells of tissue culture from which Nicotiana plants can be regenerated, plant calli, plant clumps, and plant cells that are intact in plants or parts of plants, such as pollen, flowers, embryos, ovules, seeds, pods, leaves, stems, roots, anthers and the like. Thus, another aspect of this invention is to provide for cells which upon growth and differentiation produce a cultivar having essentially all of the physiological and morphological characteristics of Nicotiana Interspecific Hybrid.

Culture for expressing desired structural genes and cultured cells are known in the art. Also as known in the art, Nicotiana are transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich, et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in Methods in Plant Molecular Biology & Biotechnology, Glich, et al., (Eds. pp.67–88 CRC Press, 1993); and by Phillips, et al., "Cell-Tissue Culture and In-Vitro Manipulation" in Corn & Corn Improvement, 3rd Edition; Sprague, et al., (Eds. pp. 345–387) American Society of Agronomy Inc., 1988. Methods of introducing expression vectors into plant tissue include the direct infection or co-cultivation of plant cells with *Agrobacterium tumefaciens,* Horsch et al., Science, 227:1229 (1985). Descriptions of Agrobacterium vectors systems and methods for Agrobacterium-mediated gene transfer provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device Agrobacterium-medicated transformation. Transformant plants obtained with the protoplasm of the invention are intended to be within the scope of this invention.

The present invention contemplates a Nicotiana plant regenerated from a tissue culture of a variety or hybrid plant of the present invention. As is well known in the art, tissue culture of Nicotiana can be used for the in vitro regeneration of a Nicotiana plant. Tissue culture of various tissues of Nicotiana and regeneration of plants therefrom is well known and widely published. For example, reference may be had to Weissbach and Weissbach (eds.), Meth. Enzymol. 118 (1986); Zaitlin et al. (eds), Biotechnology in Plant Science (1985).

When the term Nicotiana plant is used in the context of the present invention, this also includes any single gene conversions of that variety. The term single gene converted plant as used herein refers to those Nicotiana plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term backcrossing as used herein refers to the repeated crossing of a hybrid progeny back to the recurrent parent. The parental Nicotiana plant which contributes the gene for the desired characteristic is termed the nonrecurrent or donor parent. This terminology refers to the fact that the nonrecurrent parent is used one time in the backcross protocol and therefore does not recur. The parental Nicotiana plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a Nicotiana plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus.

DEPOSIT INFORMATION

A deposit of the Nicotiana seed of this invention has been made with the American Type Culture Collection, Manassas, Va. The deposit was made on Jul. 12, 1999 and has ATCC Accession No. PTA-323.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method of producing interspecific Nicotiana hybrids comprising:
   a. selecting a first parental line for a high level of biomass in one species;
   b. selecting a second parental line of another species which is capable of a high level of systemic expression of heterologous protein from transfection by a viral vector;
   c. crossing a high biomass first parent with a high expression level second parent to produce an interspecific hybrid;
   d. selecting a chromosome-doubled hybrid and;
   e. harvesting the resultant seed.

2. The resultant seed of claim 1, wherein said seed produces plants having both a high level biomass and the capacity for high level of systemic expression of heterologous protein from transfection by a viral vector.

3. Tissue culture of the seed of claim 2.

4. A Nicotiana plant regenerated from the tissue culture of claim 3.

5. A Nicotiana plant, or its parts, produced by growing the seed of claim 2.

6. Tissue culture of regenerable cells of the plant, or its parts, of claim 5.

7. The tissue culture of claim 6, wherein the regenerable cells are embryos, meristematic cells, pollen, leaves, anthers, roots, root tips, flower, seeds, stems, or protoplasts or calli derived therefrom.

8. A Nicotiana plant regenerated from the tissue culture of claim 7.

9. Pollen of the plant of claim 5.

10. An ovule of the plant of claim 5.

11. A Nicotiana plant having essentially all of the physiological and morphological characteristics of the Nicotiana plant of claim 5, or its parts.

12. A method for producing a Nicotiana seed comprising crossing a first parent Nicotiana plant with a second parent Nicotiana plant and harvesting the resultant hybrid Nicotiana seed, wherein said first or second parent Nicotiana plant is the Nicotiana plant of claim 5.

13. A hybrid Nicotiana seed produced by the method of claim 12.

14. A hybrid Nicotiana plant, or its parts, produced by growing said hybrid Nicotiana seed of claim 13.

15. Nicotiana seed produced from said hybrid Nicotiana plant of claim 14.

16. The Nicotiana plant , or its parts, produced from the Nicotiana seed of claim 15.

17. The Nicotiana plant of claim 5, further comprising a single gene conversion.

18. The single gene conversion of the Nicotiana plant of claim 17, where the gene is a transgenic gene.

19. The single gene conversion of the Nicotiana plant of claim 17, where the gene is a dominant allele.

20. The single gene conversion of the Nicotiana plant of claim 17, where the gene is a recessive allele.

21. The single gene conversion Nicotiana plant of claim 17, where the gene confers herbicide resistance.

22. The single gene conversion of the Nicotiana plant of claim 17, where the gene confers insect resistance.

23. The single gene conversion of the Nicotiana plant of claim 17, where the gene confers resistance to bacterial, fungal or viral disease.

24. The single gene conversion of the Nicotiana plant of claim 17, where the gene confers male sterility.

25. The single gene conversion of the Nicotiana plant of claim 17, where the gene confers improved nutritional quality.

26. A hybrid seed produced from the method of claim 1, wherein said first parental line is TW47 and said second parental line is TW16 which is deposited as ATCC Accession No. PTA-323.

27. The method of claim 1, wherein said first parental line is TW47.

28. The method of claim 1, wherein said second parental lines is TW16.

29. The method of claim 1, wherein said chromosome-doubled hybrid is selected after treatment using colchicine or mid vein regeneration.

30. A method of producing backcross progeny from interspecific Nicotiana hybrids comprising:
   a. selecting one parent of an interspecific hybrid as a recurrent parent which is capable of a high level of systemic expression of heterologous protein from transfection by a viral vector;
   b. backcrossing said interspecific hybrid to said recurrent parent to produce progeny;
   c. backcrossing the progeny of step b to the recurrent parent to produce resultant progeny;
   d. selecting said resultant progeny from step c for both a biomass greater than the recurrent parent and having a capacity for systemic protein expression from a viral vector greater than the primary interspecific hybrid;
   e. repeating steps c–d with said selected progeny until the selected traits of biomass and systemic protein expression breed true;
   f. collecting seed from the resultant progeny of step e.

31. A resultant seed produced from the method of claim 30, wherein said seed produces plants having both a high level biomass and the capacity for high level of systemic expression of heterologous protein from transfection by a viral vector.

32. A Nicotiana plant, or its parts, produced by growing the seed of claim 31.

33. Tissue culture of regenerable cells of the plant, or its parts, of claim 32.

34. The tissue culture of claim 33, wherein the regenerable cells are embryos, meristematic cells, pollen, leaves, anthers, roots, root tips, flower, seeds, stems, or protoplasts or calli derived therefrom.

35. A Nicotiana plant regenerated from the tissue culture of claim 34.

36. Pollen of the plant of claim 32.

37. An ovule of the plant of claim 32.

38. A Nicotiana plant having essentially all of the physiological and morphological characteristics of the Nicotiana plant of claim 32, or its parts.

39. A method of producing backcross progeny from interspecific Nicotiana hybrids comprising:
   a. selecting one parent of an interspecific hybrid as a recurrent parent based on biomass greater than the primary interspecific hybrid;
   b. backcrossing said interspecific hybrid to said recurrent parent;
   c. backcrossing the resulting progeny of step b to the recurrent parent;
   d. selecting progeny from step c for capacity for systemic protein expression from a viral vector greater than the recurrent parent and a level of biomass greater than the primary interspecific hybrid;
   e. repeating steps c–d with said selected progeny until the selected traits of biomass and systemic protein expression breed true; and
   f. collecting seed from the resulting progeny of step e.

40. The seed produced from the method of claim 39.

41. A Nicotiana plant, or its parts, produced by growing the seed of claim 40.

42. A Nicotiana plant having essentially all of the physiological and morphological characteristics of the Nicotiana plant of claim 41, or its parts.

43. Tissue culture of the seed of claim 42.

44. A Nicotiana plant regenerated from the tissue culture of claim 43.

45. Pollen of the plant of claim 41.

46. An ovule of the plant of claim 41.

47. Tissue culture of regenerable cells of the plant, or its parts, of claim 41.

48. A tissue culture of claim 47, wherein the regenerable cells are selected from the group consisting of: embryos, meristematic cells, pollen, leaves, anthers, roots, root tips, flower, seeds, stems, protoplasts and calli derived therefrom.

49. A Nicotiana plant regenerated from the tissue culture of claim 48.

50. A method of producing backcross progeny from interspecific Nicotiana hybrids comprising:
   a. selecting one parent of an interspecific hybrid as a recurrent parent based on biomass greater than the primary interspecific hybrid;
   b. backcrossing said interspecific hybrid to said recurrent parent;
   c. selfing the resulting progeny of step b;
   d. selecting self progeny from step c for biomass greater than the recurrent parent and a capacity for systemic protein expression from a viral vector greater than the primary interspecific hybrid;
   e. repeating steps c–d with said self progeny until the selected traits of biomass and systemic protein expression breed true;
   f. collecting seed from the resulting progeny of step e.

51. The seed produced from the method of claim 50.

52. A Nicotiana plant, or its parts, produced by growing the seed of claim 51.

53. Tissue culture of regenerable cells of the plant, or its parts, of claim 52, wherein said regenerable cells are selected from the group consisting of: embryos, meristematic cells, pollen, leaves, anthers, roots, root tips, flower, seeds, stems, or protoplasts or calli derived therefrom.

54. A Nicotiana plant regenerated from the tissue culture of claim 53.

55. A Nicotiana plant having essentially all of the physiological and morphological characteristics of the Nicotiana plant of claim 52, or its parts.

* * * * *